United States Patent [19]

Weeks

[11] Plant 4,003

[45] Jan. 4, 1977

[54] ROSE PLANT

[76] Inventor: O. L. Weeks, 926 W. Philadelphia, Ontario, Calif. 91761

[21] Appl. No.: 656,654

[22] Filed: Feb. 9, 1976

[51] Int. Cl.[2] ..... A01H 5/00
[52] U.S. Cl. ..... Plt./19
[58] Field of Search ..... Plt./18–19

*Primary Examiner*—Robert E. Bagwill
*Attorney, Agent, or Firm*—Frank B. Robb

CLAIM

A new distinct variety of rose plant of the hybrid tea class, substantially as herein shown and described, characterized particularly as to novelty by the unique combination of a very vigorous, upright and very symmetrical habit of growth; large-leafed and waxy foliage; very large and many-petaled flowers; a distinctive and attractive soft pink flower color; and an extraordinary flower fragrance in the nature of a heavy permeating perfume.

1 Drawing Figure

1

The present invention relates to a new and distinct variety of rose plant of the hybrid tea class, which was originated by me by crossing two unnamed and unpatented rose seedlings of rather complex breedings, and which are respectively identified in my breeding records as No. 6525-A-7 and No. 6531-A-5, the former being the seed parent and the latter being the pollen parent.

As the result of this breeding, I have produced a new and improved rose variety which is distinguished from its parents, as well as from all other rose varieties of which I am aware, as evidenced by the following unique combination of principal characteristics which are outstanding in the new variety:

1. A very vigorous, upright and very symmetrical habit of growth;
2. Large-leafed and waxy foliage;
3. Very large and many-petaled flowers;
4. A distinctive and attractive soft pink flower color; and
5. An extraordinary flower fragrance in the nature of a heavy permeating perfume.

In comparison with its seed parent, the flowers of this parent are more reddish pink, whereas the flower color of my new variety is a paler, softer and more pleasing pink shade. While the flowers of this parent also have a heavy fragrance, those of my new variety are larger in size and have a much greater substance which is lacking in the flowers of this parent.

As compared with the pollen parent, the flowers of this parent are of a deeper pink shade and have flower petals which are of considerably larger size individually than those of the new variety, with the petals being heavier and more waxy than those of the new variety. While the flowers of the pollen parent are also very fragrant and a strong fragrance has been inherited by the new variety from both parents, the flower color of both parents is noticeably deeper in shade than the soft pink flower color of the new variety.

Asexual reproduction of my new rose variety by budding, as performed by me at Chino, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

2

The following is a detailed description of my new variety, with color terminology in accordance with Munsell's Color Cascade, published by Munsell Color Company, Inc., of Baltimore, Md., except where general color terms of ordinary dictionary significance are obvious:

Type: Hardy; fairly tall; bush; outdoor; seedling; for cut flowers and for garden decoration.

Class: Hybrid tea.

Breeding: Seedling.

*Seed parent.*—An unnamed seedling.

*Pollen parent.*—An unnamed seedling.

Propagation: Holds its distinguishing characteristics through succeeding propagations by budding.

FLOWERS

Locality where grown and observed: Chino, Calif.

Flowers borne: Singly and two or three to stem; in regular clusters; on normally strong stems of medium length.

Quantity of bloom: Free and abundant, both outdoors and in greenhouse.

Continuity: From intermittent to continuous.

Fragrance: Exceptionally strong.

Bud:

*Peduncle.*—Medium length; from medium to heavy caliper; erect; fairly smooth; with numerous yellow hairs a few prickles. Color—Yellowish green.

*Before calyx breaks.*—Size—From medium to large. Form—Medium length; pointed; mostly oval; with foliaceous appendages on the surface of the bud; with stout, bristle-like foliaceous parts extending beyond the tip of the bud equal to ½ or more of its length. Color—Light Green, 22-9, turning to darker Green, 22-14 toward foliaceous parts at the top.

*As petals first open.*—Size—From medium to large. Form—Medium long and mostly flat. Color—Outside—Deep Pinkish Red, 40-13. Inside—Light Pinkish Red, 40-9. Opening—Opens up well.

Bloom:

*Size (when fully open).*—From medium to large; from 3½ inches to 4 inches.

*Petalage.*—Very double (many petals, usually with no stamens showing); from 40 to 45 petals; arranged regularly.

*Form.*—Fairly flat, open, full, slightly high-centered and globular at first, but becoming flat;

petals at first being tightly cupped and rolled slightly outward, but later becoming loosely rolled slightly outward at maturity.

Petals:

*Texture.*—Moderately thick and soft.

*Appearance.*—Inside—Velvety. Outside—Satiny-velvety.

*Shape.*—Outside—Mostly obovate; lightly scalloped; with slightly rounded apex. Intermediate—Obovate; not scalloped; with slightly rounded apex. Inside—Obovate; not scalloped; with slightly pointed apex and with one or two notches.

This description of a newly opened flower as made from a rose grown outdoors in the month of September at Ontario, Calif.:

Color:

*Outer petal.*—Outside surface—Very light Yellow, 25-2, blending quickly upward to pale Pink, 41-3, with a heavier tint of Pink, 42-6 around the edges. Inside surface—Very light pale Yellow, 26-2, blending quickly upward to pale Pink, 41-4, then shaded to a darker Pink, 41-6 about half way up, with the border at the top being deep reddish Pink, 41-9.

*Intermediate petal.*—Outside surface—Light Yellow, 25-3, blending quickly upward into pale Pink, 40-3, which continues upward to become bordered with a ¼ inch band of darker Pink, 40-6. Inside surface—Light Yellow, 25-3, blending quickly upward into pale Pink 40-3 and blending further upward to a slightly darker Pink, 40-6 around the edges.

*Inner petal.*—Outside surface—Lemon Yellow, 25-3, quickly blending upward into light Pink, 40-4, and continuing upward blending to a medium light Pink, 40-5, with an occasional single white streak running up center of petal. Inside surface—Lemon Yellow, 25-3, blending upward to a pale Pink, 40-3, and blending further upward to a slightly darker Pink, 40-5, with occasional single white streak running up center of petal.

This description was made from a rose that was open for three days outdoors during the month of September at Ontario, Calif.:

Color:

*Outer petal.*—Outside surface—Medium light Yellow, 26-2, blending upward to a light pale Pink 41-2, then to a darker Pink 42-5 near the edge. Inside surface—medium to light Yellow at the bottom, shading slowly upward into a pale Pink, 41-3, and then blending to a darker Pink, 41-9 around the edges.

*Inner petal.*—Outside surface—Lemon Yellow, 27-3, blending shortly into medium light Pink, 40-3, then blending upward to medium Pink, 39-5 at the edges. Inside surface—Lemon Yellow, 27-3, turning into light Pink, 41-2, then darkening to a medium Pink, 40-4 near the top edge, with no change in the border.

*General color effect.*—Newly opened flower—Shades of medium dark Pink, 40-6, blending downward toward the center to a lighter shade of Pink, 40-3. 3-days open—Shades of medium dark Pink, 41-9 on upper portion of petals, blending downward to a lighter Pink, 41-2 toward the bottom.

*Behavior.*—Drop off cleanly.

*Flower longevity.*—On bush in garden—4 or 5 days in September. Cut roses grown outdoors and kept at living room temperatures 3 or 4 days in September.

REPRODUCTIVE ORGANS

Stamens: From few to medium number; arranged regularly about pistils; tucked in calyx.

Filaments: From medium length to long; most with anthers.

*Color.*—Mostly Yellow, with some brown ones.

Anthers: From medium to large size; open at various times.

*Color.*—Dark Yellow.

Pollen: Sparse.

*Color.*—Yellow.

Pistils: Many.

Styles: Even; from medium length to long; medium caliper; bunched; columnar.

Stigma:

*Color.*—Pinkish Red.

Ovaries: All enclosed in calyx.

Hips: None observed.

Sepals: Permanent; medium length; straight; curled and recurved.

*Color.*—From medium to dark Green.

Seeds: None observed.

PLANT

Foliage:

*Leaves.*—Compound of 3–5 leaflets; very abundant; moderately large; moderately heavy and leathery.

*Leaflets.*—Shape—Ovate, with apex obtuse, and with margin finely serrate.

*Color.*—Mature—Upper surface—Moderately light Yellowish Green. Under surface—Light Green. Young—Upper surface—Moderately light Yellowish Green. Under surface—Light Green.

*Rachis (the supporting stem of the compounds leaf).*—From medium weight to heavy. Upper side—Smooth; grooved; slightly hairy. Under side—Smooth.

*Stipules.*—From medium length to long; moderately narrow; with long points turning out at an angle of 45°.

Disease and Insect Resistance: Above average good resistance to powdery mildew and normal good resistance to usual rose insects under field grown conditions, as determined by comparison with other rose varieties grown under the same conditions at Ontario, Calif.

Growth:

*Habit.*—Moderately tall; bushy; upright; much-branched.

*Growth.*—Vigorous.

*Canes.*—From medium to heavy caliper.

*Main stems.*—Color—Medium Green. Large prickles—Many; medium length; straight; with long, broad base. Color—Chocolate Brown. Small prickles—Several. Color—Brown. Hairs—None. prickles—

*Branches.*—Color—Dull Yellowish Green. Large prickles—Several; from medium length to long; straight; with long, broad base. Color—Chocolate Brown. Small prickles—Several. Color—Dark Brown. Hairs—None.

*New shoots.*—Color—Reddish Green. Large prickles—Several; from medium length to long; hooked slightly downward; with long narrow base. Color—Brownish Red. Small prickles—Several. Color—Reddish Brown. Hairs—None.

I claim:

1. A new and distinct variety of rose plant of the hybrid tea class, substantially as herein shown and described, characterized particularly as to novelty by the unique combination of a very vigorous, upright and very symmetrical habit of growth; large-leafed and waxy foliage; very large and many-petaled flowers; a distinctive and attractive soft pink flower color; and an extraordinary flower fragrance in the nature of a heavy permeating perfume.

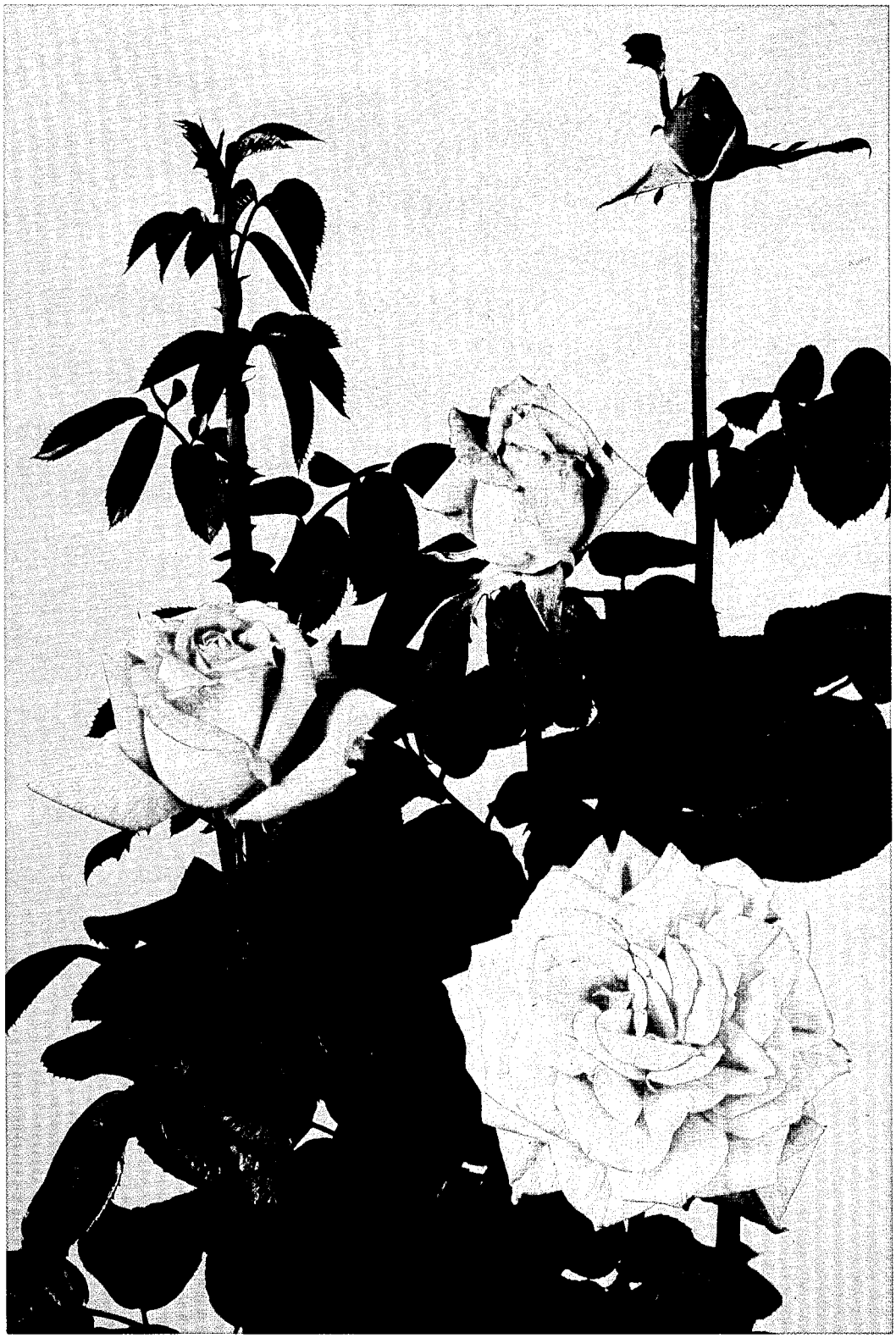

* * * * *